(12) United States Patent
Shinal

(10) Patent No.: US 6,268,524 B1
(45) Date of Patent: Jul. 31, 2001

(54) METHOD FOR PREPARATION OF DISODIUM PAMIDRONATE

(75) Inventor: Edward C. Shinal, Holmdel, NJ (US)

(73) Assignee: Aesgen, Inc., Princeton, NJ (US)

( * ) Notice: Subject to any disclaimer, the term of this patent is extended or adjusted under 35 U.S.C. 154(b) by 0 days.

(21) Appl. No.: 09/639,366

(22) Filed: Aug. 15, 2000

Related U.S. Application Data

(63) Continuation of application No. 09/209,153, filed on Dec. 10, 1998.

(51) Int. Cl.$^7$ ........................................................... C07F 9/38
(52) U.S. Cl. ................................................................. 562/13
(58) Field of Search .................................. 562/16, 13, 17, 562/11, 8

(56) References Cited

U.S. PATENT DOCUMENTS

| | | | |
|---|---|---|---|
| 3,962,432 | 6/1976 | Schmidt-Dunker | 424/204 |
| 4,142,916 | * 3/1979 | Ogasa et al. | |
| 4,304,734 | 12/1981 | Jary et al. | 260/502.5 |
| 4,327,039 | 4/1982 | Blum et al. | 260/502.5 |
| 4,439,194 | 3/1984 | Harwood et al. | 604/890 |
| 4,513,891 | 4/1985 | Hain et al. | 222/213 |
| 4,639,338 | 1/1987 | Stahl et al. | 260/502.5 |
| 4,711,880 | 12/1987 | Stahl et al. | 514/108 |
| 4,797,388 | 1/1989 | Francis | 514/23 |
| 4,814,326 | 3/1989 | Rosini et al. | 514/108 |
| 4,816,259 | 3/1989 | Matthews et al. | 424/463 |
| 4,922,007 | 5/1990 | Kieczykowski et al. | 562/13 |
| 5,096,717 | 3/1992 | Wirth et al. | 424/490 |
| 5,139,786 | 8/1992 | Ferrini et al. | 424/449 |
| 5,159,108 | 10/1992 | Kieczykowski | 562/13 |
| 5,296,475 | 3/1994 | Flesch et al. | 514/108 |
| 5,344,825 | 9/1994 | Khanna et al. | 514/108 |
| 5,366,965 | 11/1994 | Strein | 514/102 |
| 5,403,829 | 4/1995 | Lehtinen et al. | 514/102 |
| 5,431,920 | 7/1995 | Bechard | 424/480 |
| 5,449,819 | 9/1995 | Venkataramani et al. | 562/13 |
| 5,650,165 | 7/1997 | Akemi et al. | 424/448 |
| 5,780,055 | 7/1998 | Habib et al. | 424/464 |
| 5,785,985 | 7/1998 | Czech et al. | 424/448 |
| 5,888,550 | 3/1999 | Cook et al. | 424/490 |
| 5,932,240 | 8/1999 | D'Angelo et al. | 424/449 |

FOREIGN PATENT DOCUMENTS

| | | | |
|---|---|---|---|
| 19820974 | 11/1999 | (DE) | C07F/9/38 |
| 0177443 | 8/1984 | (EP) | C07F/9/38 |
| 88/00829 | 2/1988 | (WO) | A61K/31/66 |

OTHER PUBLICATIONS

Bentley's "Textbook of Phamaceuticals" Eighth Edition edited by Rawlins pp 186–194, 1977.*
English translation of "Angewandte Biopharmazie" ed by Ritschel p.12 (submitted p 1 +12), 1973.*
CA:75:91517 abs of Pharmazie by Huettehrauch et al 26(7), pp 438 1971.*
"Aredia (R)—Pamidronate Disodium for Injection", *Physicians' Desk Reference, 52nd Edition*, Arky, R., (ed.), Medical Economics Company, Inc., Montvale, N.J., p. 1824–1828, (1998).
"CA:111:28530 abs if WO8800829", (Feb. 1998).
Cooper, J., "Quality Control of Plastic Pharmaceutical Containers", *Cron. Farm., 14 (1)*, Abstract, CAPLUS Document No. 75:40273, pp. 19–27, (1971).
Nicklin, P.L., et al., "Development of a Minimum–Calcuium Caco–2 Monolayer Model: Calcium and Magnesium Ions Retard the Transport of Pamidronate", *Int. J. Pharm., 123 (2)*, Abstract, CAPLUS Document No. 123:1319687, pp. 187–197, (1995).
Su, G., et al., "Preparation of amino–diphosphinic acid and its sodium salts as bone absorption inhibitors", *Chemical Abstracts, 128 (10)*, Abstract No. 115081, 1 p., (Mar. 9, 1998).

\* cited by examiner

Primary Examiner—Jean F. Vollano
(74) Attorney, Agent, or Firm—Schwegman, Lundberg, Woessner & Kluth, P.A.

(57) ABSTRACT

The invention provides amorphous disodium pamidronate having no more than about 1–2 wt-% water.

2 Claims, No Drawings

METHOD FOR PREPARATION OF DISODIUM PAMIDRONATE

This application is a continuation of U.S. patent application Ser. No. 09/209,153, filed on Dec. 10, 1998, which is incorporated herein by reference.

BACKGROUND OF THE INVENTION

Disodium 3-amino-1-hydroxypropane-1,1-diphosphoniate or "disodium pamidronate" has the formula:

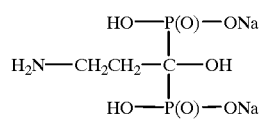

It is commercially available as the lyophilized pentahydrate, under the name AREDIA® from Novartis Pharmaceuticals Corp., and is used to inhibit bone resorption, i.e., to treat moderate or severe hypercalcemia associated with malignancy, with or without bone metastases. The preparation of the crystalline pentahydrate from pamidronic acid is disclosed by Stahl et al. in U.S. Pat. Nos. 4,711,880 and 4,639,338. This material is prepared by partially neutralizing a heated slurry of pamidronic acid with aqueous sodium hydroxide (NaOH) to pH 7–7.5 and then initiating crystallization at $\geq 50°$ C. The mixture is slowly cooled to 0–5° C. and the disodium pamidronate is collected by filtration. This product is described as having "excellent crystallinity" and as being "completely stable to storage under approximately normal ambient conditions." It comprises about 24.1–25% water.

The crystalline product ("Modification E") is contrasted with an amorphous product disclosed to be prepared by the general process of Jary et al. (U.S. Pat. No. 4,304,734). In Comparison Example 1 of the '338 patent, pamidronic acid is neutralized to pH 7.4 with aqueous NaOH and the reaction mixture is concentrated to dryness under reduced pressure at 60–70° C. and then dried at 20 mbar to constant weight. However, the amorphous product that is obtained is described as deliquescent in air, contains 12.9% of retained water and, as taught in the '338 patent, will convert to the pentahydrate. Stahl et al. also teach the interconversion of other crystalline forms of disodilum pamidroniate depending upon humidity and amount of water present, which demonstrates the difficulty in utilizing preformed disodium salts of pamidronic acid for further processing into sterile pharmaceutical dosage forms.

Thus, a need exists for a simple method to prepare disodium pamidronate that is stable to storage and suitable for reconstitution and intravenous infusion/injection.

SUMMARY OF THE INVENTION

The present invention provides a method for the preparation of amorphous, essentially anhydrous ($\leq 1-2$ wt-% water) disodium pamidronate (the "product"). The product of the invention can be stored under nitrogen at otherwise ambient conditions, and readily reconstituted with sterile water or physiological salt solutions for injection or infusion into a patient in need of treatment therewith.

The method comprises addition of aqueous sodium hydroxide to a stirred slurry of pamidronic acid in an about 2:1 molar ratio of NaOH to acid, optionally comprising excess mannitol, to yield a clear solution of pH 6.5±0.1. Aqueous phosphoric acid is added as needed if the pH following NaOH addition is too high. A small amount of aqueous NaOH can be added if the pH is too low. Preferably, 1 N aqueous NaOH is used.

The solution is frozen and lyophilized under reduced pressure to yield amorphous, essentially anhydrous disodium pamidronate. The product is stable when stored under dry nitrogen at otherwise ambient conditions.

Preferably, the about pH 6.5 solution is filtered and aliquots are introduced into suitable container(s), then frozen (−25 to −40° C.), lyophilized (10–25 mbar, 20–40° C.) in situ, and the containers sealed under positive nitrogen pressure to yield a plurality of unit dosage forms of disodium pamidronate, optionally in admixture with mannitol.

For example, vials containing 30 mg, 60 mg and 90 mg of sterile lyophilized disodium pamidronate, each optionally containing 470 mg, 400 mg, and 375 mg of mannitol can readily be prepared and utilized as disclosed in *Physician's Desk Reference* (52d ed., 1988) at pages 1824–1828.

As used herein, the term "about" incorporates inherent variability of the parameter referenced, due to measurement techniques known to the art, i.e., pH, or water content (loss on drying).

DETAILED DESCRIPTION OF THE INVENTION

The invention will be further described by reference to the following detailed example.

EXAMPLE 1

Preparation of Disodium Pamidronate

For a batch size of 5 L, 587.5 g (3.2 moles) of mannitol is dissolved in 3.5 L of water. Pamidronic acid (31.6 g, 0.133 moles) is mixed with a 1.0 L aliquot of the matinitol solution to form a slurry. The slurry is then transferred into the remainder of the mannitol solution, and stirred for at least 15 min. Aqueous 1N sodium hydroxide (270 ml) is then added and the mixture is stirred until a clear, colorless solution results. The pH is then adjusted to 6.5±0.1 using either 1M aqueous phosphoric acid or 1N aqueous sodium hydroxide, as needed. The solution is then filtered through a 0.22 micron filter, and filled at 20° C. into vials at 4.0 ml (4.172 g)/vial, under sterile conditions. The aqueous solution is frozen at −37° C. and lyophilized (20 mbar, 20–40° C.) to yield 1,250 vials, each containing 30 mg of amorphous disodium pamidronate. The vials are sealed under positive nitrogen pressure. The disodium pamidronate is amorphous (noncrystalline) by X-ray diffraction and contains 0.7 wt-% water (USP 23 <731>).

Alternatively, the present product can be formulated for oral administration as disclosed, for example, in Bechard (U.S. Pat. No. 5,431,920) or Strein (U.S. Pat. No. 5,366,965).

All publications, patents and patent documents are incorporated by reference herein, as through individually incorporated by reference. The invention has been described with reference to various specific and preferred embodiments and techniques. However, it should be understood that many variations and modifications may be made while remaining within the spirit and scope of the invention.

What is claimed is:

1. Amorphous, essentially anhydrous disodium pamidronate that contains $\leq 2$ wt-% water.

2. Amorphous, essentially anhydrous disodium pamidronate that contains $\leq 1$ wt-% water.

\* \* \* \* \*

UNITED STATES PATENT AND TRADEMARK OFFICE
CERTIFICATE OF CORRECTION

PATENT NO. : 6,268,524 B1
DATED : July 31, 2001
INVENTOR(S) : Shinal et al.

Page 1 of 1

It is certified that error appears in the above-identified patent and that said Letters Patent is hereby corrected as shown below:

Column 1,
Line 10, delete "diphosphoniate" and insert -- diphosphonate --, therefor.
Line 45, delete "disodilum pamidroniate" and insert -- disodium pamidronate --, therefor.

Column 2,
Line 34, delete "matinitol" and insert -- mannitol --, therefor.

Column 2, claim 1,
Line 62, delete ", essentially anhydrous".

Column 2, claim 2,
Line 64, delete ", essentially anhydrous".

Signed and Sealed this

Ninth Day of April, 2002

Attest:

*Attesting Officer*

JAMES E. ROGAN
*Director of the United States Patent and Trademark Office*